United States Patent
Zhao et al.

(10) Patent No.: US 11,781,110 B2
(45) Date of Patent: Oct. 10, 2023

(54) INDUCTION OF CORNEAL ENDOTHELIAL CELLS

(71) Applicant: The Regents of the University of California, Oakland, CA (US)

(72) Inventors: Jiagang Zhao, San Diego, CA (US); Natalie Afshari, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 328 days.

(21) Appl. No.: 16/096,756

(22) PCT Filed: May 1, 2017

(86) PCT No.: PCT/US2017/030408
§ 371 (c)(1),
(2) Date: Oct. 26, 2018

(87) PCT Pub. No.: WO2017/190136
PCT Pub. Date: Nov. 2, 2017

(65) Prior Publication Data
US 2019/0119633 A1    Apr. 25, 2019

Related U.S. Application Data

(60) Provisional application No. 62/329,467, filed on Apr. 29, 2016.

(51) Int. Cl.
| | |
|---|---|
| *C12N 5/00* | (2006.01) |
| *C12N 5/079* | (2010.01) |
| *A61K 35/30* | (2015.01) |
| *G01N 33/50* | (2006.01) |
| *C12N 5/0797* | (2010.01) |
| *A61P 27/02* | (2006.01) |
| *C12N 5/0735* | (2010.01) |
| *C12N 5/074* | (2010.01) |

(52) U.S. Cl.
CPC ............ *C12N 5/0621* (2013.01); *A61K 35/30* (2013.01); *A61P 27/02* (2018.01); *C12N 5/0037* (2013.01); *C12N 5/0606* (2013.01); *C12N 5/0623* (2013.01); *C12N 5/0696* (2013.01); *G01N 33/5064* (2013.01); *C12N 2500/99* (2013.01); *C12N 2501/15* (2013.01); *C12N 2501/155* (2013.01); *C12N 2501/415* (2013.01); *C12N 2501/727* (2013.01); *C12N 2506/45* (2013.01)

(58) Field of Classification Search
CPC .............................. C12N 5/0621; A61K 35/30
See application file for complete search history.

(56) References Cited

U.S. PATENT DOCUMENTS 10,220,117 B2 *   3/2019   Zhang ..................... A61L 27/26
2011/0081719 A1    4/2011   Gamm et al.
2014/0370007 A1   12/2014   McCabe et al.

OTHER PUBLICATIONS

Chen, B., Dodge, M.E., Tang, W., Lu, J., Ma, Z., Fan, C.-W., Wei, S., Hao, W.., 30 Kilgore, J., Williams, N.S., et al. (2009), "Small molecule-mediated disruption of Wnt-dependent signaling in tissue regeneration and cancer", Nat Chem Biol 5, 100-107. (Year: 2009).*
Lamba, D.A., Karl, M.O., Ware, C.B., and Reh, T.A. (2006), "Efficient generation of retinal progenitor cells from human embryonic stem cells", Proc. Natl. Acad. Sci. U.S. A. 103, 12769-12774. (Year: 2006).*
Lamba, D.A., McUsic, A., Hirata, R.K., Wang, P.-R., Russell, D., and Reh, T.A. (2010), "Generation, purification and transplantation of photoreceptors derived from human induced pluripotent stem cells", PloS One 5, e8763. (Year: 2010).*
Zuber, M.E., Gestri, G., Viczian, A.S., Barsacchi, G., and Harris, W.A. (2003), "Specification of the vertebrate eye by a network of eye field transcription factors", 35 Dev. Camb. Engl. /30, 5155-5167. (Year: 2003).*
Yang et al., "The evolving roles of canonical WNT signaling in stem cells and tumorigenesis: implications in targeted cancer therapies", Laboratory Investigation, 2016, vol. 96, pp. 116-136. (Year: 2016).*
PCT International Search Report and Written Opinion for PCT/US2017/030408 dated Sep. 14, 2017 (10 pages).
Zhang et al., "Isolation and Transportation of Corneal Endothelial Cell-Like Cells Derived from In-Vitro-Differentiated Human Embryonic Stem Cells," Stem Cells and Development, 2014, 23:1340-1354.
Zhao et al., "Generation of Human Corneal Endothelial Cells via In Vitro Ocular Lineage Restriction of Pluripotent Stem Cells," IOVS, 2016, 57(15):6878-6884.

* cited by examiner

*Primary Examiner* — Laura Schuberg
(74) *Attorney, Agent, or Firm* — Eversheds Sutherland (US) LLP (57) ABSTRACT

Compositions and methods for producing major ocular cell types, including retinal ganglion cells, photoreceptors, retinal pigmented epithelium and corneal endothelial cells, from human pluripotent stem cells under defined culture conditions are provided.

7 Claims, 6 Drawing Sheets

INDUCTION OF CORNEAL ENDOTHELIAL CELLS

CROSS REFERENCE TO RELATED APPLICATIONS

This application claims the priority benefit of PCT/US2017/030408 filed on May 1, 2017 which claims priority benefit to U.S. Provisional Patent Application Ser. No. 62/329,467 filed on Apr. 29, 2016, the entire contents of which are hereby incorporated by reference.

FIELD OF THE INVENTION

Ocular degenerative diseases including age-related macular degeneration (AMD), retinitis pigmentosa, glaucoma, and corneal endothelial dystrophy (CED) cause irreversible vision loss and affect millions of people worldwide. Currently, there is no effective drug intervention. Grafting healthy eye cells to replenish the diseased tissues such as retina represents a promising therapeutic approach (Zarbin, 2016). However, previous attempts at using primary human eye cells have met with limited success due to the limited expansion capacity and differentiation potential of adult progenitors or difficulty of obtaining sufficient human fetal retinal progenitors, and possible ethical concerns. Human pluripotent stem cells (PSCs), including human embryonic stem cells (ESCs), and induced pluripotent stem cells (iPSCs) represent promising renewable donor sources for cell-based replacement therapy. Nevertheless, PSCs themselves are not suitable for direct transplantation in clinical applications due to their tendency to form teratomas and low efficiency in repopulating host tissues with desirable reprogrammed cell types in vivo.

Thus, major efforts have focused on production of differentiated derivatives of hPSCs such as neural retinal progenitor cells (Banin et al., 2006; Lamba et al., 2006), retinal pigment epithelium (RPE) (Buchholz et al., 2009; Klimanskaya et al., 2004; Vugler et al., 2008), photoreceptors (Gonzalez-Cordero et al., 2013; Lamba et al., 2010; Osakada et al., 2008), and corneal endothelial cells (CECs) (McCabe et al., 2015; Zhang et al., 2014). While the advancement of clinical trials of hESC-derived RPE transplants for treatment of patients with Stargardt's macular dystrophy and AMD (Schwartz et al., 2012, 2015) is encouraging to the field, there is a great need for methods of generating unlimited other specialized eye cells effectively in vitro for treating blindness due to the loss of photoreceptors, RGCs and CECs.

Although the presumptive eye field cells have not been isolated in culture, evidence from earlier works of experimental embryology involving transplantation support the notion that there is an eye field cell population in the anterior neural plate of vertebrate embryos (Adelmann, 1936; Li et al., 1997). More recently, the self-organization of a 3D optic cup derived from mouse and human embryonic stem cells further demonstrates that the initially formed optical cup-like structure may harbor primitive eye field stem cells, (Eiraku et al., 2011a; Meyer et al., 2009; Nakano et al., 2012). These cells may be responsible for driving an intrinsic eye morphogenesis program. Two major developmental signaling gradients, Wnt and BMP, have been shown to play major roles in shaping the eye field within the primitive anterior neuroepithelium (del Barco Barrantes et al., 2003; Cavodeassi et al., 2005).

SUMMARY OF THE INVENTION

The present invention provides that by applying a small molecule-driven differentiation approach, the pluripotent state of human PSCs can be uniformly restricted to a primitive neuroepithelial eye field state. Further studies indicate that this cell population has characteristics of tissue stem cells, and this cell population is referred to herein as human eye field stem cells (EFSCs). PSC-derived EFSCs can be directed to differentiate toward either retina or neural crest lineages after they are given inductive cues in culture. In addition, EFSCs have the capacity to integrate into recipient retinas after transplantation.

Eye cell fate specification was carried out under defined small molecule-driven conditions and in a stepwise fashion of lineage specification. During the initial phase, PSC fate was restricted to the eye field-like state and became eye field stem cell (EFSC). In the second phase, PSC-derived EFSC was further committed toward retinal lineage or ocular neural crest lineage. The retinal sublineage specification gave rise to retinal pigmented epithelium (RPE), photoreceptor and retinal ganglion cell (RGC) by inducing EFSC using the different combinations of chemical modulators accordingly. The formation of CEC sheet was directly induced from ocular neural crest stem cell (NCSC) by suppressing TGFβ and ROCK signaling in the culture.

Under chemically defined conditions, PSCs were massively converted into EFSCs and subsequently NCSCs. Eye field cell identity was characterized by the expression of key transcription factors. Over 80% of cells were positive for both PAX6 and LHX2, two critical fate restriction factors for early eye field cells. Cell identity was further confirmed by detection of an elevated expression of early eye field transcription factors via qPCR. The induction of ocular NCSCs was initiated by promoting WNT signaling in EFSCs. Within two weeks of induction, the majority of cells expressed the typical neural crest markers p75NTR and HNK-1. EFSC-derived NCSCs can be propagated and cryopreserved. Finally, CEC sheet formation was induced from adherent NCSCs in the presence of a ROCK inhibitor. The polygonal shaped CEC-like cells became visible after a week in culture. The expression of typical CEC markers such as ZO-1, N-cadherin and Na+/K+-ATPase were also detected.

Unlike previously reported induction procedures, the present methods utilize a novel small molecule-based approach to derive human CECs along with three major retinal cell types, RPE, photoreceptor and RGC, from PSCs in a directional fate restriction fashion. Moreover, using EFSC-derived NCSCs as a starting cell source cell, CECs can be quickly and directly induced and expanded in culture.

BRIEF DESCRIPTION OF THE DRAWINGS

FIGS. 1A-1C show induction of EFSCs from human PSCs.

FIGS. 2A-2C show EFSCs can be specified to the fate of retinal ganglion cells (RGCs) under chemically defined culture conditions. FIG. 2A shows EFSCs can differentiate into RGCs with high efficiency. After two weeks of culture under conditions for RGC induction, differentiated cells displayed long neuronal processes and expressed typical RGC markers such as BRN3 (red) and TUJ1 (green). Cell nuclei were counterstained with Hoechst 33342 (blue).

FIGS. 3A-3B show characterization of EFSC differentiation to either neuronal or non-neuronal retinal cell fates under defined culture conditions.

FIGS. 4A-4C show induction of neural crest stem cells (NCSCs) from PSCs in vitro. The cells were stained positively for two typical NCSC markers HNK-1 (red, FIG. 4A) and p75NTR (green, FIG. 4B). FIG. 4A, 200 um; FIG. 4B and FIG. 4C, 50 μm.

FIGS. 5A-5C show morphology and characterization of human NCSC-derived CECs.

DETAILED DESCRIPTION OF THE INVENTION

I. Overview

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the term "pluripotent" refers to a cell that has the potential to differentiate into any of the three germ layers: endoderm, mesoderm, and ectoderm.

As used herein, the term "multipotent" refers to a cell that is not terminally differentiated.

As used herein, "cell population" refers to a number of cells obtained from any suitable source. The cell population may be cultured in vitro. Those of ordinary skill in the art will appreciate that there are various methods for culturing cell populations for use with the present invention and various numbers of cells that are suitable for use in the present invention.

As used herein, "marker" or "biomarker" refers generally to a DNA, RNA, protein, carbohydrate, or glycolipid-based molecular marker, the expression or presence of which in a cultured cell population can be detected by standard methods (or methods disclosed herein) and is consistent with one or more cells in the cultured cell population having a characteristic or phenotype. The marker may be a polypeptide expressed by the cell or an identifiable physical location on a chromosome, such as a gene, a restriction endonuclease recognition site or a nucleic acid encoding a polypeptide (e.g., an mRNA) expressed by the native cell. The marker may be an expressed region of a gene referred to as a "gene expression marker", or some segment of DNA with no known coding function. The biomarkers may be cell-derived, e.g., secreted, products.

The terms "differentially expressed gene," "differential gene expression" and their synonyms, which are used interchangeably, refer to a gene whose expression is activated to a higher or lower level in a first cell or cell population, relative to its expression in a second cell or cell population. The terms also include genes whose expression is activated to a higher or lower level at different stages over time during passage of the first or second cell in culture. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between the first cell and the second cell. Differential expression includes both quantitative, as well as qualitative, differences in the temporal or cellular expression pattern in a gene or its expression products among, for example, the first cell and the second cell. "Differential gene expression" is considered to be present when there is a difference between the expression of a given gene in the first cell and the second cell. A marker may be differentially expressed.

As used herein, "inhibit", "down-regulate", "under-express" and "reduce" are used interchangeably and mean that the expression of a gene, or level of RNA molecules or equivalent RNA molecules encoding one or more proteins or protein subunits, or activity of one or more proteins or protein subunits, is reduced relative to one or more controls, such as, for example, one or more positive and/or negative controls.

As used herein, "up-regulate" or "over-express" is used to mean that the expression of a gene, or level of RNA molecules or equivalent RNA molecules encoding one or more proteins or protein subunits, or activity of one or more proteins or protein subunits, is elevated relative to one or more controls, such as, for example, one or more positive and/or negative controls.

As used herein, the term "differentiation regulator agent" refers to any compound or molecule that regulates cellular differentiation. A "negative differentiation regulator agent" refers to any compound or molecule that inhibits a pluripotent cell or a multipotent cell from following a differentiation pathway. A "positive differentiation regulator agent" refers to any compound or molecule that induces a pluripotent cell or a multipotent cell to follow a differentiation pathway into a more differentiated cell phenotype.

As used herein, the term "cell differentiation environment" refers to a cell culture condition wherein cells are induced to differentiate into a more differentiated cell type. The cell differentiation environment can include, for example, an adherent culture of cells. The term "adherent culture" refers to a cell culture system whereby cells are cultured on a solid surface, which may in turn be coated with a substrate. The cells may or may not tightly adhere to the solid surface or to the substrate. The substrate for the adherent culture may further comprise, for example, any one or combination of polyornithine, laminin, poly-lysine, purified collagen, gelatin, extracellular matrix, fibronectin, tenacin, vitronectin, poly glycolytic acid (PGA), poly lactic acid (PLA), poly lactic-glycolic acid (PLGA), matrigel, and feeder cell layers such as, but not limited to, primary astrocytes, astrocyte cell lines, glial cell lines, bone marrow stromal cells, primary fibroblasts or fibroblast cells lines.

As used herein, "substantially separated from" or "substantially separating" refers to the characteristic of a population of first substances being removed from the proximity of a population of second substances, wherein the population of first substances is not necessarily devoid of the second substance, and the population of second substances is not necessarily devoid of the first substance. However, a population of first substances that is "substantially separated from" a population of second substances has a measurably lower content of second substances as compared to the non-separated mixture of first and second substances. In one aspect, at least 50%, 60%, 70%, 80%, 90%, 95%, 98%, 99%, or more of the second substance is removed from the first substance.

As used herein, a composition containing a "purified cell population" or "purified cell composition" means that at least 50%, 60%, typically at least 70%, and more preferably 80%, 90%, 95%, 98%, 99%, or more of the cells in the composition are of the identified type.

As used herein, "proliferation" or "expansion" refers to the ability of a cell or population of cells to increase in number.

As used herein, "patient" or "subject" means an animal subject to be treated, with human patients being preferred.

As used herein, "therapeutically effective" refers to an amount of a substance (cells, biomolecules, etc.) that is sufficient to treat or ameliorate, or in some manner reduce the symptoms associated with a disease or condition. When used with reference to a method, the method is sufficiently effective to treat or ameliorate, or in some manner reduce the symptoms associated with a disease or condition. For example, an effective amount in reference to a disease is that amount which is sufficient to block or prevent its onset; or if disease pathology has begun, to palliate, ameliorate, stabilize, reverse or slow progression of the disease, or otherwise reduce pathological consequences of the disease. In any case, an effective amount may be given in single or divided doses.

As used herein, the term "treatment" embraces at least an amelioration of the symptoms associated with a disease or condition in the patient, where amelioration is used in a broad sense to refer to at least a reduction in the magnitude of a parameter, e.g. a symptom associated with the condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition.

As used herein, "regenerative effect" means an effect which provides a benefit to a cell or tissue. The effect may include, without limitation, a reduction in the degree of injury to a cell or tissue, or an improvement in, restoration of, or stabilization of a cell or tissue's function.

II. Methods for Producing Cell Cultures

Methods are provided for producing cell cultures. In embodiments, the methods include one or more of the following steps: (1) providing a culture of pluripotent stem cells (PSCs); (2) culturing the PSCs in a cell differentiation environment that induces PSCs to differentiate into eye field stem cells (EFSCs); (3) purifying and/or expanding the EFSCs; (4) providing a culture of EFSCs; (5) culturing the EFSCs in a cell differentiation environment that induces EFSCs to differentiate into ocular neural crest stem cells (NCSCs), retinal pigmented epithelium (RPE) cells, photoreceptor cells, or retinal ganglion cells (RGCs); (6) purifying and/or expanding the NCSCs, RPE cells, photoreceptor cells, or RGCs; (7) providing a culture of NCSCs, RPE cells, photoreceptor cells, or RGCs; (8) culturing NCSCs in a cell differentiation environment that induces NCSCs to differentiate into corneal endothelial cells (CECs); (9) purifying and/or expanding the CECs; and/or (10) providing CECs.

In some embodiments, a culture of pluripotent stem cells is provided. Pluripotent stem cells can originate from a variety of animal sources including, for example, humans. Suitable pluripotent stem cells for use in accordance with this disclosure include, for example, induced pluripotent cell (iPS cells), naïve embryonic stem cells derived from embryos (ES cells), embryonic stem cells made by somatic cell nuclear transfer (ntES cells), and embryonic stem cells from unfertilized eggs (parthenogenesis embryonic stem cells, or pES cells).

In some embodiments, pluripotent stem cells are cultured in a cell differentiation environment that induces PSCs to differentiate into eye field stem cells (EFSCs). In some embodiments, PSCs are cultured in the presence and/or absence of one or more differentiation regulator agents to induce or guide PSCs to differentiate into eye field stem cells. In some embodiments, PSCs are cultured in the presence of small molecule inhibitors of WNT and TGF-β/

BMP signaling activities, which induces PSCs to differentiate into eye field stem cells. Exemplary small molecule inhibitors can include, for example, IWP2 (WNT pathway inhibitor), LDN193189 (BMP pathway inhibitor), and SB431542 (TGF-β pathway inhibitor).

In some embodiments, culturing PSCs in a cell differentiation environment can include seeding PSCs as an adherent culture and allowing the cells to grow under feeder-free and serum-free conditions to near-confluence. The PSCs can then be cultured in the presence of a small molecule eye field differentiation cocktail that induces PSCs to differentiate into eye field stem cells. One exemplary cocktail includes eye field priming medium supplemented with IWP-LDN-SB.

In some embodiments, the culturing of PSCs in a cell differentiation environment causes at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, or more of the PSCs to become eye field stem cells. In some embodiments, the resulting eye field stem cells exhibit one or more biomarkers consistent with the EFSC phenotype. In some embodiments, the resulting eye field stem cells lack one or more biomarkers consistent with the EFSC phenotype. Exemplary EFSC biomarkers, the presence of which is consistent with the EFSC phenotype, can include eye field progenitor transcription factors (e.g. PAX6, RX, LHX2, SIX3, and SIX6), primitive neuroepithelial stem cell markers (e.g. Nestin), and markers of proliferative activity (e.g. Ki67). In embodiments, EFSC biomarkers include retinal progenitor markers. In embodiments, the expression of EFSC biomarkers is increased over 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, 500, 600, 700, 800, 900, 1000, 1100, 1200, 1300, 1400, 1500, 1600, 1700, 1800, 1900, 2000 fold, or more relative to the PSC cells from which the EFSCs are derived.

In some embodiments, EFSCs derived from PSCs are purified ex vivo. In some embodiments, the methods for producing PSC-derived EFSCs yield EFSCs with high purity and no purification is needed. For example, in some embodiments, the methods for producing PSC-derived EFSCs result in a cellular composition comprising at least 70%, 80%, 90%, 95%, 98%, 99%, or more EFSCs. In some embodiments, the methods for producing PSC-derived EFSCs yield EFSCs with low purity or less-than-desired purity, and EFSC purification is desired. In some embodiments, EFSCs are purified by substantially separating EFSCs from other cells in the composition (e.g. undifferentiated PSCs and/or PSCs that differentiated into an undesired cell lineage or phenotype). In some embodiments, purification results in a cellular composition comprising at least 70%, 80%, 90%, 95%, 98%, 99%, or more EFSCs.

In some embodiments, EFSCs derived from PSCs are expanded ex vivo. In some embodiments, ex vivo expansion of EFSCs is one of the ways to increase the number of EFSCs for subsequent use (therapy, assays, etc.). In some embodiments, EFSCs are expanded at least 2-fold, at least 3-fold, 4, 5, 6, 7, 8, 9, 10, 50, 100, 200, 300, 500, or at least 800-fold. In some embodiments, compositions comprising EFSCs contain a relevant number or population of EFSCs, depending upon the ultimate use for which the composition is intended (e.g. therapy, drug assay, etc.). In some embodiments, the compositions comprising EFSCs include about $10^3$, about $10^4$, about $10^5$ cells, about $10^6$ cells, about $10^7$ cells, about $10^8$ cells, about $10^9$ cells, about $10^{10}$ cells or more.

In some embodiments, a culture of eye field stem cells is provided. Eye field stem cells can originate from a variety of animal sources including, for example, humans. In some embodiments, eye field stem cells can be derived from PSCs using methods in accordance with this disclosure.

In some embodiments, eye field stem cells are cultured in a cell differentiation environment that induces EFSCs to differentiate into ocular neural crest stem cells (NCSCs). In some embodiments, EFSCs are cultured in the presence and/or absence of one or more differentiation regulator agents to induce or guide EFSCs to differentiate into NCSCs. One exemplary differentiation regulator agent is CHIR 99021. In some embodiments, culturing EFSCs in a cell differentiation environment can include seeding EFSCs at a low density and/or removing any prior culture media (e.g. eye field differentiation cocktail or eye field culture media). The EFSCs can then be cultured in the presence of a NCSC cocktail that induces EFSCs to differentiate into NCSCs. One exemplary cocktail includes NCSC induction medium supplemented with the presence of 3 μM CHIR 99021.

In some embodiments, the culturing of EFSCs in a cell differentiation environment causes at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, or more of the EFSCs to become NCSCs. In some embodiments, the resulting NCSCs exhibit one or more biomarkers consistent with the NCSC phenotype. In some embodiments, the resulting NCSCs lack one or more biomarkers consistent with the NCSC phenotype. Exemplary NCSC biomarkers, the presence of which is consistent with the NCSC phenotype, can include NCSC surface markers (e.g. HNK-1), enriched NGF receptor (e.g. enriched p75NTR relative to EFSCs), and expression of nuclear translocation of beta-catenin (an indication of increased WNT canonical signaling during neural crest formation). In embodiments, the expression of NCSC biomarkers is increased over 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, 500, 600, 700, 800, 900, 1000, 1100, 1200, 1300, 1400, 1500, 1600, 1700, 1800, 1900, 2000 fold, or more relative to the EFSCs from which the NCSCs are derived.

In some embodiments, NCSCs derived from EFSCs are purified ex vivo. In some embodiments, the methods for producing EFSC-derived NCSCs yield NCSCs with high purity and no purification is needed. For example, in some embodiments, the methods for producing EFSC-derived NCSCs result in a cellular composition comprising at least 70%, 80%, 90%, 95%, 98%, 99%, or more NCSCs. In some embodiments, the methods for producing EFSC-derived NCSCs yield NCSCs with low purity or less-than-desired purity, and NCSC purification is desired. In some embodiments, NCSCs are purified by substantially separating NCSCs from other cells in the composition (e.g. undifferentiated EFSCs and/or EFSCs that differentiated into an undesired cell lineage or phenotype). In some embodiments, purification results in a cellular composition comprising at least 70%, 80%, 90%, 95%, 98%, 99%, or more NCSCs.

In some embodiments, NCSCs derived from EFSCs are expanded ex vivo. In some embodiments, ex vivo expansion of NCSCs is one of the ways to increase the number of NCSCs for subsequent use (therapy, assays, etc.). In some embodiments, NCSCs are expanded at least 2-fold, at least 3-fold, 4, 5, 6, 7, 8, 9, 10, 50, 100, 200, 300, 500, or at least 800-fold. In some embodiments, compositions comprising NCSCs contain a relevant number or population of NCSCs, depending upon the ultimate use for which the composition is intended (e.g. therapy, drug assay, etc.). In some embodiments, the compositions comprising NCSCs include about $10^3$, about $10^4$, about $10^5$ cells, about $10^6$ cells, about $10^7$ cells, about $10^8$ cells, about $10^9$ cells, about $10^{10}$ cells or more.

In some embodiments, eye field stem cells are cultured in a cell differentiation environment that induces EFSCs to differentiate into retinal pigmented epithelium (RPE) cells. In some embodiments, EFSCs are cultured in the presence and/or absence of one or more differentiation regulator agents to induce or guide EFSCs to differentiate into RPE cells. One exemplary differentiation regulator agent is activin A. In some embodiments, culturing EFSCs in a cell differentiation environment can include seeding EFSCs to yield an adherent EFSC monolayer culture and/or removing any prior culture media (e.g. eye field differentiation cocktail or eye field culture media). The EFSCs can then be cultured in the presence of a RPE cell cocktail that induces EFSCs to differentiate into RPE cells. One exemplary cocktail includes RPE cell initiation medium supplemented with activin A. The SMAD signaling inhibition (via removal EFSC media) and addition of activin A can direct EFSCs toward the RPE fate because activin A and BMP activities can be important to RPE specification.

In some embodiments, the culturing of EFSCs in a cell differentiation environment causes at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, or more of the EFSCs to become RPE cells. In some embodiments, the resulting RPE cells exhibit one or more biomarkers consistent with the RPE cell phenotype. In some embodiments, the resulting RPE cells lack one or more biomarkers consistent with the RPE cell phenotype. Exemplary RPE cell biomarkers, the presence of which is consistent with the RPE cell phenotype, can include RPE65 (an RPE-specific isomerase required for the conversion of all-trans retinol to 11-cis retinal and visual pigment regeneration) and polygonal actin bundle formation inside of epithelium-like cells. In embodiments, the expression of RPE cell biomarkers is increased over 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, 500, 600, 700, 800, 900, 1000, 1100, 1200, 1300, 1400, 1500, 1600, 1700, 1800, 1900, 2000 fold, or more relative to the EFSCs from which the RPE cells are derived.

In some embodiments, RPE cells derived from EFSCs are purified ex vivo. In some embodiments, the methods for producing EFSC-derived RPE cells yield RPE cells with high purity and no purification is needed. For example, in some embodiments, the methods for producing EFSC-derived RPE cells result in a cellular composition comprising at least 70%, 80%, 90%, 95%, 98%, 99%, or more RPE cells. In some embodiments, the methods for producing EFSC-derived RPE cells yield RPE cells with low purity or less-than-desired purity, and RPE cell purification is desired. In some embodiments, RPE cells are purified by substantially separating RPE cells from other cells in the composition (e.g. undifferentiated EFSCs and/or EFSCs that differentiated into an undesired cell lineage or phenotype). In some embodiments, purification results in a cellular composition comprising at least 70%, 80%, 90%, 95%, 98%, 99%, or more RPE cells.

In some embodiments, RPE cells derived from EFSCs are expanded ex vivo. In some embodiments, ex vivo expansion of RPE cells is one of the ways to increase the number of RPE cells for subsequent use (therapy, assays, etc.). In some embodiments, RPE cells are expanded at least 2-fold, at least 3-fold, 4, 5, 6, 7, 8, 9, 10, 50, 100, 200, 300, 500, or at least 800-fold. In some embodiments, compositions comprising RPE cells contain a relevant number or population of RPE cells, depending upon the ultimate use for which the composition is intended (e.g. therapy, drug assay, etc.). In some embodiments, the compositions comprising RPE cells include about $10^3$, about $10^4$, about $10^5$ cells, about $10^6$ cells, about $10^7$ cells, about $10^8$ cells, about $10^9$ cells, about $10^{10}$ cells or more.

In some embodiments, eye field stem cells are cultured in a cell differentiation environment that induces EFSCs to differentiate into retinal ganglion cells (RGCs). In some embodiments, EFSCs are cultured in the presence and/or absence of one or more differentiation regulator agents to induce or guide EFSCs to differentiate into RGCs. In some embodiments, EFSCs are cultured in the presence of small molecule inhibitors of Notch and VEGFR signaling, which induce EFSCs to differentiate into RGCs. Exemplary small molecule inhibitors can include, for example, IWP2 (WNT pathway inhibitor), DAPT (NOTCH pathway inhibitor), and PD173074 (VEGFR pathway inhibitor). In some embodiments, culturing EFSCs in a cell differentiation environment can include seeding EFSCs to yield an EFSC culture and/or removing any prior culture media (e.g. eye field differentiation cocktail or eye field culture media). The EFSCs can then be cultured in the presence of a RGC cocktail that induces EFSCs to differentiate into RGCs. One exemplary cocktail includes RGC initiation medium supplemented with IWP2, DAPT, and PD173074.

In some embodiments, the culturing of EFSCs in a cell differentiation environment causes at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, or more of the EFSCs to become RGCs. In some embodiments, the resulting RGCs exhibit one or more biomarkers consistent with the RGC phenotype. In some embodiments, the resulting RGCs lack one or more biomarkers consistent with the RGC phenotype. Exemplary RGC biomarkers, the presence of which is consistent with the RGC phenotype, can include TUJ1, BRN3, BRN3A, BRN3B, ISL-1, and MATH5. In embodiments, the expression of RGC biomarkers is increased over 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, 500, 600, 700, 800, 900, 1000, 1100, 1200, 1300, 1400, 1500, 1600, 1700, 1800, 1900, 2000 fold, or more relative to the EFSCs from which the RGCs are derived.

In some embodiments, RGCs derived from EFSCs are purified ex vivo. In some embodiments, the methods for producing EFSC-derived RGCs yield RGCs with high purity and no purification is needed. For example, in some embodiments, the methods for producing EFSC-derived RGCs result in a cellular composition comprising at least 70%, 80%, 90%, 95%, 98%, 99%, or more RGCs. In some embodiments, the methods for producing EFSC-derived RGCs yield RGCs with low purity or less-than-desired purity, and RGC purification is desired. In some embodiments, RGCs are purified by substantially separating RGCs from other cells in the composition (e.g. undifferentiated EFSCs and/or EFSCs that differentiated into an undesired cell lineage or phenotype). In some embodiments, purification results in a cellular composition comprising at least 70%, 80%, 90%, 95%, 98%, 99%, or more RGCs.

In some embodiments, RGCs derived from EFSCs are expanded ex vivo. In some embodiments, ex vivo expansion of RGCs is one of the ways to increase the number of RGCs for subsequent use (therapy, assays, etc.). In some embodiments, RGCs are expanded at least 2-fold, at least 3-fold, 4, 5, 6, 7, 8, 9, 10, 50, 100, 200, 300, 500, or at least 800-fold. In some embodiments, compositions comprising RGCs contain a relevant number or population of RGCs, depending upon the ultimate use for which the composition is intended (e.g. therapy, drug assay, etc.). In some embodiments, the compositions comprising RGCs include about $10^3$, about $10^4$, about $10^5$ cells, about $10^6$ cells, about $10^7$ cells, about $10^8$ cells, about $10^9$ cells, about $10^{10}$ cells or more.

In some embodiments, eye field stem cells are cultured in a cell differentiation environment that induces EFSCs to differentiate into photoreceptor cells. In some embodiments, EFSCs are cultured in the presence and/or absence of one or more differentiation regulator agents to induce or guide EFSCs to differentiate into photoreceptor cells. In some embodiments, EFSCs are cultured in the presence of small molecule inhibitors and/or promoters, which induce EFSCs to differentiate into photoreceptor cells. Exemplary small molecules suitable for use in the present disclosure can include, for example, ALK4/5/7 signaling inhibitors (e.g. SB), GSK-3 signaling inhibitors (e.g. CHIR99021), Notch signaling inhibitors (e.g. DAPT), Shh signaling stimulators (purmorphamine), retinoic acid, and taurine.

In some embodiments, culturing EFSCs in a cell differentiation environment can include seeding EFSCs to yield an EFSC culture and/or removing any prior culture media (e.g. eye field differentiation cocktail or eye field culture media). The EFSCs can then be cultured in the presence of a RGC cocktail that induces EFSCs to differentiate into a small molecule photoreceptor cell cocktail that induces EFSCs to differentiate into photoreceptor cells. In one exemplary embodiment, photoreceptor cells are produced from EFSCs by first culturing EFSCs with small molecule ALK4/5/7 signaling inhibitors (e.g. SB), GSK-3 signaling inhibitors (e.g. CHIR99021), Notch signaling inhibitors (e.g. DAPT), and Shh signaling stimulators (purmorphamine), and then culturing EFSCs with a medium supplemented with retinoic acid and taurine.

In some embodiments, the culturing of EFSCs in a cell differentiation environment causes at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, or more of the EFSCs to become photoreceptor cells. In some embodiments, the resulting photoreceptor cells exhibit one or more biomarkers consistent with the photoreceptor cell phenotype. In some embodiments, the resulting photoreceptor cells lack one or more biomarkers consistent with the photoreceptor cell phenotype. Exemplary photoreceptor cell biomarkers, the presence of which is consistent with the photoreceptor cell phenotype, can include pan-photoreceptor markers (e.g. recoverin), cone cell-specific markers (e.g. OPN1SW or blue Opsin), rod cell-specific markers (e.g. rhodopsin), and markers of both rod and cone photoreceptors (e.g. human interphotoreceptor retinoid binding protein or IRBP). In embodiments, the expression of photoreceptor cell biomarkers is increased over 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, 500, 600, 700, 800, 900, 1000, 1100, 1200, 1300, 1400, 1500, 1600, 1700, 1800, 1900, 2000 fold, or more relative to the EFSCs from which the photoreceptor cells are derived.

In some embodiments, photoreceptor cells derived from EFSCs are purified ex vivo. In some embodiments, the methods for producing EFSC-derived photoreceptor cells yield photoreceptor cells with high purity and no purification is needed. For example, in some embodiments, the methods for producing EFSC-derived photoreceptor cells result in a cellular composition comprising at least 70%, 80%, 90%, 95%, 98%, 99%, or more photoreceptor cells. In some embodiments, the methods for producing EFSC-derived photoreceptor cells yield photoreceptor cells with low purity or less-than-desired purity, and photoreceptor cell purification is desired. In some embodiments, photoreceptor cells are purified by substantially separating photoreceptor cells from other cells in the composition (e.g. undifferentiated EFSCs and/or EFSCs that differentiated into an undesired cell lineage or phenotype). In some embodiments, purification results in a cellular composition comprising at least 70%, 80%, 90%, 95%, 98%, 99%, or more photoreceptor cells.

In some embodiments, photoreceptor cells derived from EFSCs are expanded ex vivo. In some embodiments, ex vivo expansion of photoreceptor cells is one of the ways to increase the number of photoreceptor cells for subsequent use (therapy, assays, etc.). In some embodiments, photoreceptor cells are expanded at least 2-fold, at least 3-fold, 4, 5, 6, 7, 8, 9, 10, 50, 100, 200, 300, 500, or at least 800-fold. In some embodiments, compositions comprising photoreceptor cells contain a relevant number or population of photoreceptor cells, depending upon the ultimate use for which the composition is intended (e.g. therapy, drug assay, etc.). In some embodiments, the compositions comprising photoreceptor cells include about $10^3$, about $10^4$, about $10^5$ cells, about $10^6$ cells, about $10^7$ cells, about $10^8$ cells, about $10^9$ cells, about $10^{10}$ cells or more.

In some embodiments, a culture of ocular neural crest stem cells is provided. Ocular neural crest stem cells can originate from a variety of animal sources including, for example, humans. In some embodiments, ocular neural crest stem cells can be derived from eye field stem cells using methods in accordance with this disclosure.

In some embodiments, ocular neural crest stem cells are cultured in a cell differentiation environment that induces NCSCs to differentiate into corneal endothelial cells (CECs). In some embodiments, NCSCs are cultured in the presence and/or absence of one or more differentiation regulator agents to induce or guide NCSCs to differentiate into CECs. In some embodiments, EFSCs are cultured in the presence of small molecule inhibitors and/or promoters, which induce NCSCs to differentiate into corneal endothelial cells (CECs). Exemplary small molecules suitable for use in the present disclosure can include, for example, inhibitors of ALK4/5/7 signaling activity (e.g. SB431542) and Rho-associated kinase (ROCK) signaling activity (e.g. H-1125, Y21632)

In some embodiments, culturing NCSCs in a cell differentiation environment can include seeding NCSCs at a low density on an FNC coated plate and/or removing any prior culture media (e.g. NCSC differentiation cocktail or NCSC culture media). The NCSCs can then be cultured in the presence of a CEC cocktail that induces NCSCs to differentiate into CECs. In one exemplary embodiment, CECs are produced from NCSCs by culturing NCSCs with a CEC induction medium (human Endothelial-SFM, 5% FBS, 0.3 mM 2-phosphate ascorbic Acid, 1% Pen/Strep) that includes small molecular inhibitors SB431542 (1 uM) and H-1125 (2.5 uM), which suppress ALK4/5/7 and Rho-associated kinase (ROCK) signaling activities, respectively. In one exemplary embodiment, CECs are produced from NCSCs by culturing NCSCs with a serum-free culture medium (human endothelial-SFM, 0.3 mM 2-phosphate ascorbic acid) that includes small molecular inhibitors SB431542 (1 uM) and either Y21632 (10 uM) or H-1125 (2.5 uM). SB431542 suppresses ALK4/5/7 signaling activity. Y21632 and H-1125 suppresses Rho-associated kinase (ROCK) signaling activity. In some embodiments, CECs produced from NCSCs are maintained in a serum-free culture medium (human endothelial-SFM, 0.3 mM 2-phosphate ascorbic acid) that includes small molecular inhibitors SB431542 (1 uM) and either Y21632 (10 uM) or H-1125 (2.5 uM). In embodiments, maintaining CECs in a serum-free culture medium can advantageously convert the cell culture into a Xeno-free and cGMP grade product for clinical applications.

In some embodiments, the culturing of NCSCs in a cell differentiation environment causes at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, or more of the NCSCs to become CECs. In some embodiments, the resulting CECs exhibit one or more biomarkers consistent with the CEC phenotype. In some embodiments, the resulting CECs lack one or more biomarkers consistent with the CEC phenotype. Exemplary CEC biomarkers, the presence of which is consistent with the CEC phenotype, can include tight junction protein 1 (TJP1/ZO-1), N-Cadherin, and Na+/K+ ATPase. In embodiments, the expression of CEC biomarkers is increased over 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, 500, 600, 700, 800, 900, 1000, 1100, 1200, 1300, 1400, 1500, 1600, 1700, 1800, 1900, 2000 fold, or more relative to the NCSCs from which the CECs are derived.

In some embodiments, CECs derived from NCSCs are purified ex vivo. In some embodiments, the methods for producing NCSC-derived CECs yield CECs with high purity and no purification is needed. For example, in some embodiments, the methods for producing NCSC-derived CECs result in a cellular composition comprising at least 70%, 80%, 90%, 95%, 98%, 99%, or more CECs. In some embodiments, the methods for producing NCSC-derived CECs yield CECs with low purity or less-than-desired purity, and CEC purification is desired. In some embodiments, CECs are purified by substantially separating CECs from other cells in the composition (e.g. undifferentiated NCSCs and/or NCSCs that differentiated into an undesired cell lineage or phenotype). In some embodiments, purification results in a cellular composition comprising at least 70%, 80%, 90%, 95%, 98%, 99%, or more CECs.

In some embodiments, CECs derived from NCSCs are expanded ex vivo. In some embodiments, ex vivo expansion of CECs is one of the ways to increase the number of CECs for subsequent use (therapy, assays, etc.). In some embodiments, CECs are expanded at least 2-fold, at least 3-fold, 4, 5, 6, 7, 8, 9, 10, 50, 100, 200, 300, 500, or at least 800-fold. In some embodiments, compositions comprising CECs contain a relevant number or population of CECs, depending upon the ultimate use for which the composition is intended (e.g. therapy, drug assay, etc.). In some embodiments, the compositions comprising CECs include about $10^3$, about $10^4$, about $10^5$ cells, about $10^6$ cells, about $10^7$ cells, about $10^8$ cells, about $10^9$ cells, about $10^{10}$ cells or more.

In some embodiments, PSCs, EFSCs, NCSCs, RPE cells, photoreceptor cells, RGCs, and/or CECs can originate from a variety of animal sources including, for example, humans. In some embodiments, PSCs, EFSCs, NCSCs, RPE cells, photoreceptor cells, RGCs, and/or CECs can originate from a person to be treated (i.e. autologous PSCs, EFSCs, NCSCs, RPE cells, photoreceptor cells, RGCs, and/or CECs). In some embodiments, PSCs, EFSCs, NCSCs, RPE cells, photoreceptor cells, RGCs, and/or CECs can be immunocompatible with a person to be treated (i.e. allogenic PSCs, EFSCs, NCSCs, RPE cells, photoreceptor cells, RGCs, and/or CECs).

In some embodiments, PSCs, EFSCs, NCSCs, RPE cells, photoreceptor cells, RGCs, and/or CECs are maintained in culture for about 1 day to about 3 months. In some embodiments, PSCs, EFSCs, NCSCs, RPE cells, photoreceptor cells, RGCs, and/or CECs are maintained in culture for about 1 day to about 2 months. In some embodiments, PSCs, EFSCs, NCSCs, RPE cells, photoreceptor cells, RGCs, and/or CECs are maintained in culture for about 1, 2, 3, 4, 5, 6, 7, 8, 9, 10, 11, 12, 13, 14, 15, 16, 17, 18, 19, 20, 25, 30, 35, 40, 45, 50, 55, 60, or more days.

In some embodiments, compositions comprising PSCs, EFSCs, NCSCs, RPE cells, photoreceptor cells, RGCs, and/or CECs are provided. In some embodiments, compositions comprising substantially purified PSCs, substantially purified EFSCs, substantially purified NCSCs, substantially purified RPE cells, substantially purified photoreceptor cells, substantially purified RGCs, and/or substantially purified CECs are provided. In some embodiments, the PSCs, EFSCs, NCSCs, RPE cells, photoreceptor cells, RGCs, and/or CECs are autologous or allogenic.

Compositions comprising PSCs, EFSCs, NCSCs, RPE cells, photoreceptor cells, RGCs, and/or CECs can be provided to any suitable person or entity such as, for example, a patient, a clinician treating the patient, a biologic bank, a researcher, and the like. In some embodiments, compositions comprising PSCs, EFSCs, NCSCs, RPE cells, photoreceptor cells, RGCs, and/or CECs are non-naturally occurring. In some embodiments, compositions comprising PSCs, EFSCs, NCSCs, RPE cells, photoreceptor cells, RGCs, and/or CECs are not naturally occurring because the PSCs, EFSCs, NCSCs, RPE cells, photoreceptor cells, RGCs, and/or CECs are the result of one or more of purification, expansion, differentiation, isolation, and the like.

In some embodiments, a therapeutic composition comprising a therapeutically effective dose of PSCs, EFSCs, NCSCs, RPE cells, photoreceptor cells, RGCs, and/or CECs is provided. In some embodiments, a therapeutic composition comprising a therapeutically effective dose of substantially purified substantially purified PSCs, substantially purified EFSCs, substantially purified NCSCs, substantially purified RPE cells, substantially purified photoreceptor cells, substantially purified RGCs, and/or substantially purified CECs is provided.

III. Uses of Cellular Compositions

Methods are provided for treating an ocular disease in a subject. In some embodiments, a subject is identified as requiring an ocular-disease treating composition. A subject can require an ocular-disease treating composition to treat an ocular disease or symtpoms thereof such as, for example, age-related macular degeneration (AMD), retinitis pigmentosa, glaucoma, and corneal endothelial dystrophy (CED). In some embodiments, the ocular disease has caused irreversible vision loss in the subject. In some embodiments, the ocular-disease treating composition is effective to treat irreversible vision loss. In some embodiments, the ocular-disease treating composition is effective to repopulate diseased tissue (e.g. retina) in the subject with healthy ocular cells.

In some embodiments, the methods include administering to a subject with an ocular disease a composition comprising a therapeutically effective dose of EFSCs, NCSCs, RPE cells, photoreceptor cells, RGCs, and/or CECs. In some embodiments, the ocular disease is age-related macular degeneration (AMD), retinitis pigmentosa, glaucoma, or corneal endothelial dystrophy (CED). In some embodiments, the ocular disease has caused irreversible vision loss in the subject. In some embodiments, the EFSCs, NCSCs, RPE cells, photoreceptor cells, RGCs, and/or CECs are immunologically compatible with the subject (e.g. allogenic or autologous). In some embodiments, the EFSCs, NCSCs, RPE cells, photoreceptor cells, RGCs, and/or CECs were cultured in a feeder-free and serum-free defined media. In some embodiments, about $10^4$-$10^{11}$ cells can be administered in a volume of a 5 µl to 1 liter, 5 ml to 250 ml, or 50 ml to 150 ml.

In some embodiments, a therapeutically effective amount of EFSCs, NCSCs, RPE cells, photoreceptor cells, RGCs, and/or CECs can be administered to a subject with a pharmaceutically acceptable carrier. Administration routes may include any suitable means, including, but not limited to, topical application to an ocular site, injection into an ocular site, grafting at an ocular site, and the like. In some embodiments, the particular mode of administration selected will depend upon the particular treatment, disease state or condition of the patient, the nature or administration route of other drugs or therapeutics administered to the subject, etc.

In some embodiments, EFSCs, NCSCs, RPE cells, photoreceptor cells, RGCs, and/or CECs can be administered to a subject in a single dose or in several doses over selected time intervals, e.g., to titrate the dose. In some embodiments, administration of EFSCs, NCSCs, RPE cells, photoreceptor cells, RGCs, and/or CECs induces an ocular healing process. In some embodiments, administration of EFSCs, NCSCs, RPE cells, photoreceptor cells, RGCs, and/or CECs replenishes diseased tissues. In some embodiments, the administration of EFSCs, NCSCs, RPE cells, photoreceptor cells, RGCs, and/or CECs has a regenerative effect on damaged or diseased ocular tissue.

In some embodiments, the methods include administering to a subject with an ocular disease a composition comprising a therapeutically effective dose of corneal endothelial cells (CECs). In some embodiments, the corneal endothelial cells are derived from ocular neural crest stem cells. In some embodiments, the corneal endothelial cells are derived from ocular neural crest stem cells that have been derived from eye field stem cells. In some embodiments, the corneal endothelial cells are derived from ocular neural crest stem cells that have been derived from eye field stem cells that have been derived from pluripotent stem cells. In some embodiments, the ocular disease is age-related macular degeneration (AMD), retinitis pigmentosa, glaucoma, or corneal endothelial dystrophy (CED). In some embodiments, the ocular disease has caused irreversible vision loss in the subject. In some embodiments, the corneal endothelial cells are immunologically compatible with the subject (e.g. allogenic or autologous). In some embodiments, the corneal endothelial cells were cultured in a feeder-free and serum-free defined media. In some embodiments, about $10^4$-$10^{11}$ cells can be administered in a volume of a 5 µl to 1 liter, 5 ml to 250 ml, or 50 ml to 150 ml.

In some embodiments, a therapeutically effective amount of corneal endothelial cells can be administered to a subject with a pharmaceutically acceptable carrier. Administration routes may include any suitable means, including, but not limited to, topical application to an ocular site, injection into an ocular site, grafting at an ocular site, and the like. In some embodiments, the particular mode of administration selected will depend upon the particular treatment, disease state or condition of the patient, the nature or administration route of other drugs or therapeutics administered to the subject, etc.

In some embodiments, corneal endothelial cells can be administered to a subject in a single dose or in several doses over selected time intervals, e.g., to titrate the dose. In some embodiments, administration of corneal endothelial cells induces an ocular healing process. In some embodiments, administration of corneal endothelial cells replenishes diseased tissues. In some embodiments, administration of corneal endothelial cells has a regenerative effect on damaged or diseased ocular tissue.

Methods for drug discovery and/or drug screening are provided. Assays for drug discovery and/or drug screening are also provided. In embodiments, the methods include administering a drug candidate to a cell culture comprising EFSCs, NCSCs, RPE cells, photoreceptor cells, RGCs, and/or CECs, and detecting a pharmacokinetic response of the cell culture to the drug candidate. Detection of the pharmacokinetic response can identify whether the drug candidate has suitable properties (toxicity, therapeutically effective). In some embodiments, the cell culture is a culture of corneal endothelial cells. In some embodiments, the cell culture is a feeder-free and serum-free culture of corneal endothelial cells. In some embodiments, the corneal endothelial cells are derived from ocular neural crest stem cells. In some embodiments, the corneal endothelial cells are derived from ocular neural crest stem cells that have been derived from eye field stem cells. In some embodiments, the corneal endothelial cells are derived from ocular neural crest stem cells that have been derived from eye field stem cells that have been derived from pluripotent stem cells. In some embodiments, the methods can be used to determine cell health and viability in the presence of a drug candidate. In some embodiments, the methods can be used to test the toxicity a drug candidate. In some embodiments, the methods can be used to assess changes in the phenotype of a cell population in the presence of a drug candidate.

IV. Examples

A. Overview

During the early stages of embryonic brain development, eye field formation is under the influence of Wnt and BMP signaling gradients (del Barco Barrantes et al., 2003; Cavodeassi et al., 2005). The gradient of Wnt signaling is important in establishing forebrain and midbrain identities. Downregulation of Wnt signaling leads to formation of the forebrain, where the eye field resides. Accordingly, treating human ESC-derived embryoid bodies with Dkk1, a potent Wnt inhibitor, and noggin, a BMP antagonist, promotes the development of an eye field (Lamba et al., 2006; Reh et al., 2010). In addition, under dual SMAD inhibition by exposure to SB431542 (a selective and potent inhibitor of the transforming growth factor-beta [TGF-β] superfamily type I activin receptor-like kinases ALK-4, -5, and -7) and LDN193189 (a selective inhibitor of BMP type I receptors ALK-2 and ALK-3, a noggin analog), ESCs are likely to become forebrain/eye field precursors that strongly express PAX6 and LHX2, two key early transcription factors responsible for eye field formation (Chambers et al., 2009; Kriks et al., 2011).

Figure 1A:
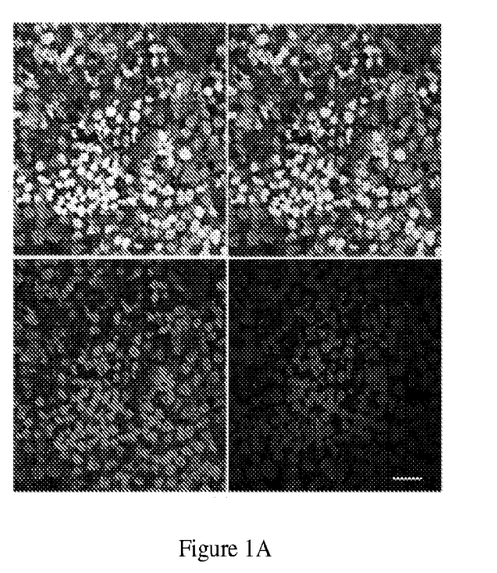
FIG. 1A shows confocal images of immunofluorescence double staining of typical early eye field transcription factors PAX6 (green) and LHX2 (red) in EFSCs derived from PSCs after one week of induction. Cell nuclei were counterstained with Hoechst 33342 (blue).
Figure 1B:
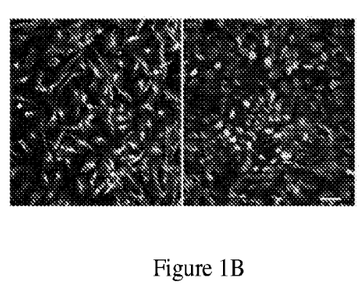
FIG. 1B shows EFSCs stained for the neuroectodermal cell marker NESTIN (white) and proliferation marker Ki67 (green).
Figure 1C:
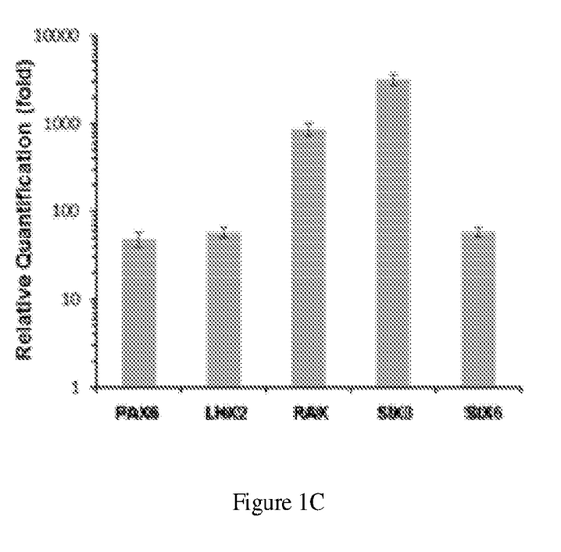
FIG. 1C shows real-time qPCR analysis of the induced expression of a panel of early eye field transcription factor genes. Scale bars=30 μm.

Therefore, as detailed in this disclosure, a chemically defined culture protocol to induce the differentiation of human PSCs toward eye field identity under synergistic inhibition of WNT and TGF-0/BMP signaling activities using the small molecule inhibitors IWP2 (Inhibitor of Wnt Production-2, a Dkk1 analog), LDN193189, and SB431542 (referred to hereafter as IWP, LDN, and SB, respectively) (Chen et al., 2009) was developed. The PSCs were seeded onto matrigel-coated plates and cultured under feeder-free and serum-free conditions to near-confluence. Subsequently, the culture was switched to eye field priming medium supplemented with the IWP-LDN-SB small molecule cocktail for one week. Under this treatment, the PSCs were converted into EFSCs en masse. The induction of EFSCs was confirmed by immunocytochemical labeling of key early eye field transcription factors (Lamba et al., 2006; Zuber et al., 2003). Over 90% of cells were positive for both PAX6 and LHX2, two key transcription factors expressed by eye field progenitors (FIG. 1B). Most PSC-derived EFSCs also expressed nestin, a typical marker of primitive neuroepithelial stem cells (FIG. 1C). In addition, the PSC-derived EFSCs retained proliferative activity as evidenced by strong expression of Ki67 (FIG. 1C). The induction of EFSCs was further confirmed by real-time PCR to assess the expression of typical early eye field transcription factor genes including PAX6, RX, LHX2, SIX3, and SIX6. Over 20- to 1200-fold increased expression of these retinal progenitor markers in EFSCs after six days of induction (FIG. 1D) was found. The expression levels of these genes were maintained over at least two passages in culture.

Figure 2A:
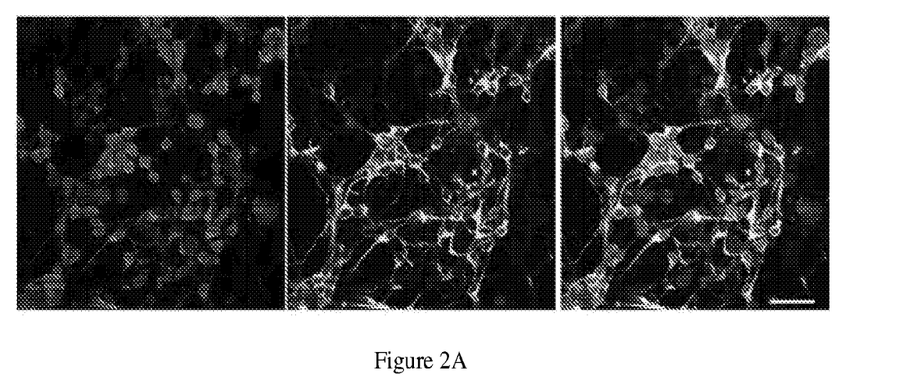
Figure 2B:
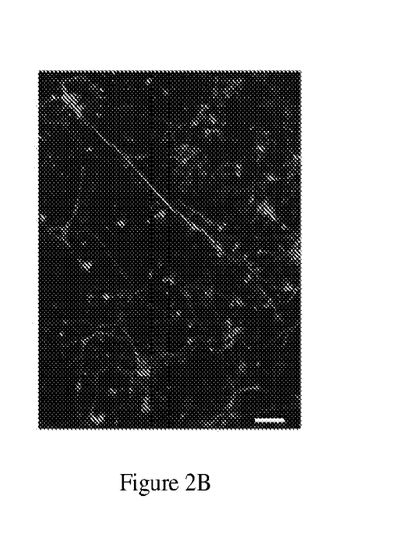
FIG. 2B shows the retinal ganglion cells differentiated from EFSCs for three weeks expressed typical marker TUJ1 (red) and exhibited long processes.
Figure 2C:
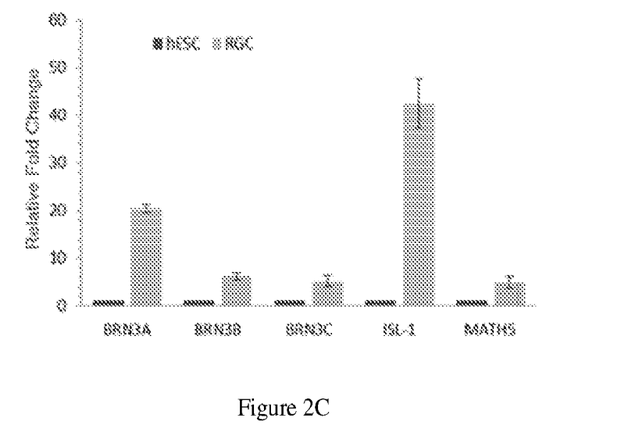
FIG. 2C shows real-time qPCR analysis for expression of RGC-specific transcription factors in cells differentiated from EFSCs.

Directed differentiation of retinal ganglion cells from PSC-derived EFSCs. To investigate whether EFSCs have the potential to give rise to different sub-lineages of eye cells in culture, a small molecule-based approach to mimic the inductive cues present in early eye development was taken. EFSCs were directed to differentiate toward specific retinal cell fates in vitro. Retinal ganglion cells (RGCs) are a major type of retinal neuron and play a critical role in transmitting visual signals from the retina to several regions of the brain. It was first tested whether EFSCs could be instructed to differentiate into RGCs directly under chemically defined conditions. Previous results demonstrate that inhibition of Notch and VEGFR signaling is important for RGC specification (Austin et al., 1995; Hashimoto et al., 2006). A cocktail of small molecule inhibitors including IWP2, DAPT, and PD173074 that could inhibit the activities of WNT, NOTCH, and VEGFR signaling, respectively, was formulated. The treatment rapidly converted EFSCs to a RGC fate. After two weeks of induction, the majority of cells were positive for both TUJ1 and BRN3, markers of RGCs (FIG. 2A). Long axon-like processes were observed after extended differentiation in culture (~3 weeks) (FIG. 2B). Quantitative PCR analysis showed remarkable upregulation of RGC precursor-specific transcription factor genes, such as BRN3A, BRN3B, ISL-1, and MATH5, after the first six days of induction (FIG. 2C).

Figure 3A:
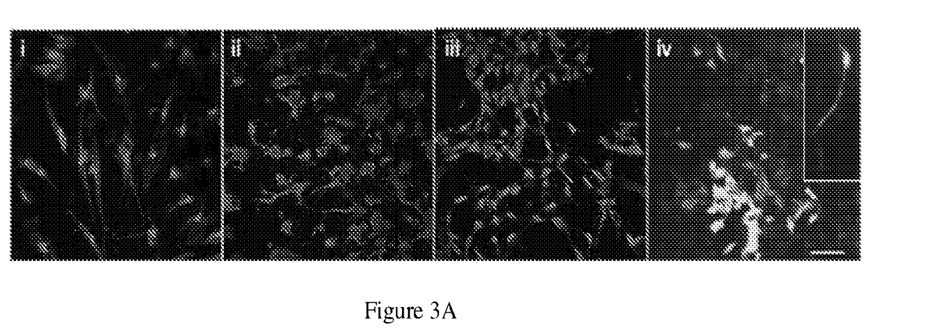
FIG. 3A shows photoreceptor induction as evidenced by immunocytochemical detection of recovering (i, red), blue opsin (OPN1SW) (ii, red), and rhodopsin (iii, red), as well as the expression of the photoreceptor-specific reporter IRBP-GFP (iv, green); a well-differentiated photoreceptor showed the typical morphology with a long outer process and short inner process (iv, inset).

Directed differentiation of photoreceptors from EFSCs. Photoreceptors are a major cell type in the retina and are responsible for the initiation of visual signal transduction. A modified in vitro photoreceptor differentiation method based on a previous report (Osakada et al., 2008) was developed, and utilized small molecules to direct the differentiation process. The restriction of photoreceptor fate from EFSCs was achieved with a two-step process. During the initial phase, EFSCs were treated with the small molecule inhibitors SB, CHIR99021, and DAPT to suppress ALK4/5/7, GSK-3, and Notch signaling activities respectively. Furthermore, the Shh signaling pathway was stimulated by the addition of purmorphamine (Sinha and Chen, 2006). Robust cell growth and proliferation, but not expression of photoreceptor-specific markers, were observed during this initial phase as previously described (Czekaj et al., 2012). During the second phase, the culture was shifted to medium supplemented with retinoic acid and taurine as described previously (Osakada et al., 2008), which induced morphological changes including extension of cellular processes in some cells after one week. To identify the fate of these differentiated cells, the expression of photoreceptor-specific markers was examined by immunocytochemistry. By day 14 after the initial induction, the pan-photoreceptor marker recoverin, cone cell-specific marker OPN1SW or blue Opsin, and rod cell-specific marker rhodopsin (FIG. 3A) were detected. To determine whether photoreceptors differentiated from EFSCs in vitro also express human interphotoreceptor retinoid binding protein (IRBP), a marker of both rod and cone photoreceptors (Eisenfeld et al., 1985), EFSCs were infected with an IRBP-GFP lentivirus and the transduced cells were differentiated toward the photoreceptor fate. This approach has been shown to specifically mark photoreceptors in transgenic mice and in human, mouse, and chick retinal explants (Lamba et al., 2010; Yokoyama et al., 1992). After 12 days of differentiation, GFP-positive cells started to appear. By day 16, clusters of GFP-expressing photoreceptors were clearly visible (FIG. 3A, iv). After further maturation, EFSC-derived photoreceptors displayed typical morphological features such as short inner processes and long extended outer processes, similar to an outer segment (FIG. 3A, iv inset).

Figure 3B:
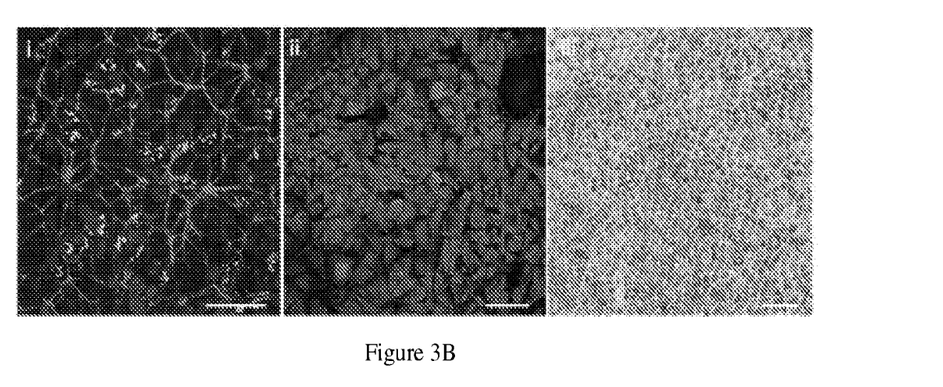
FIG. 3B shows RPE induction; (i) RPE formation as demonstrated by the early expression of RPE65 (green) and phalloidin staining the polygonal shape of RPE cells (red); (ii) elevated RPE65 expression observed after three weeks in culture (red); (iii) pigmented RPE appeared after prolonged maturation in culture. Cell nuclei were counterstained with Hoechst 33342 (blue). Scale bars=30 μm.

Directed differentiation of retinal pigment epithelium (RPE) from EFSCs. The RPE, a monolayer of cells between the neural retina and choriocapillaris, is the first committed retinal cell type to appear in the outer layer of the early optic cup (Müller et al., 2007). To test whether EFSCs were also capable of differentiating into non-neuronal RPE cells, small molecule inhibitors were withdrawn from the adherent EFSC monolayer culture and culturing conditions were shifted to RPE initiation medium as previously described (Idelson et al., 2009). The removal of SMAD signaling inhibition and addition of activin A were important for directing EFSC toward the RPE fate because activin A and BMP activities are required for RPE specification (Fuhrmann et al., 2000; Idelson et al., 2009; Müller et al., 2007). After 12 days of induction, low expression levels of RPE65, an RPE-specific isomerase required for the conversion of all-trans retinol to 11-cis retinal and visual pigment regeneration, and the formation of polygonal actin bundles were observed inside of epithelium-like cells (FIG. 3B left). Increased expression of RPE65 (FIG. 3B middle) and pigmentation of RPE (FIG. 3B right) were detected after further maturation in culture.

Figure 4A:
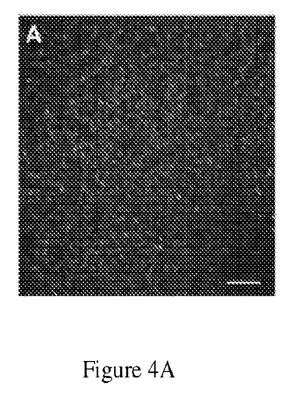
Figure 4B:
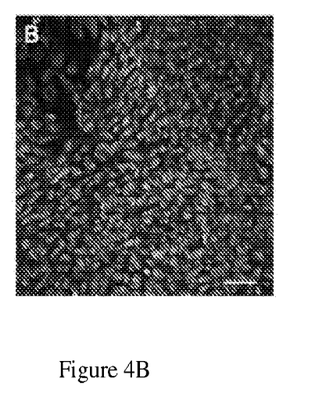
Figure 4C:
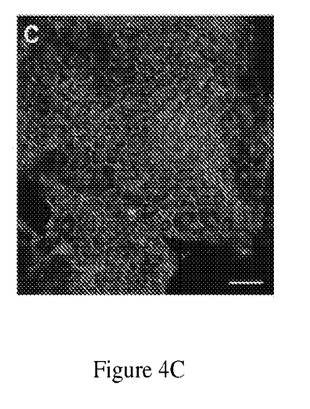
FIG. 4C shows immunostaining for the nuclear translocation of beta-catenin (green), an indication of increased Wnt signaling. Cell nuclei were counterstained with Hoechst 33342. Scale bars.

Directed differentiation of eye field stem cells into ocular neural crest stem cells. Previous studies on fate maps in bird and mammalian eyes demonstrated that the corneal endothelium is derived solely from neural crest cells in the optic region (Gage et al., 2005; Zhang et al., 2014). The in vitro derivation of neural crest stem cells from PSCs has been previously described (Chambers et al., 2013; Lee et al., 2007). It was reasoned that, if EFSCs could be primed toward ocular neural crest lineage, the cells could serve as a direct and renewable source to generate CECs in culture. To direct EFSCs toward neural crest fate, EFSCs were seeded at low density, and neural crest lineage specification was initiated in NCSC induction medium supplemented with the presence of 3 µM CHIR 99021. After a week of induction, the majority of EFSCs start to express a typical NCSC surface marker HNK-1 (FIG. 4A). The subsequent analysis of EFSC-derived NCSCs showed the enrichment of NGF receptor (p75NTR)-expressing NCSCs in the culture (FIG. 4B). Immunostaining also detected the expression of nuclear translocation of beta-catenin (FIG. 4C), an indication of increased WNT canonical signaling during neural crest formation.

Figure 5A:
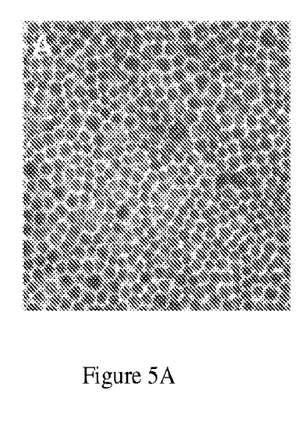
FIG. 5A is a representative phase-contrast micrograph of a confluent monolayer of human NCSC-derived CECs with a light treatment with accutase. Immuno-fluorescent images of NCSC-derived CECs which express Na/K-ATPase (red, FIG. 5B) and N-cadherin (green, FIG. 5C), two indicative markers of the corneal endothelium. Cell nuclei were counterstained with Hoechst 33342. Scale bar: 50 μm.
Figure 5B:
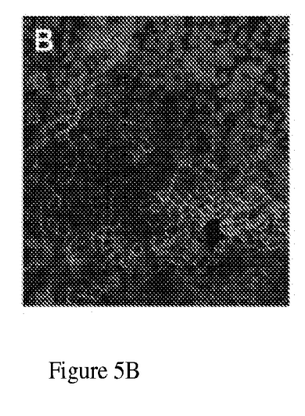
Figure 5C:
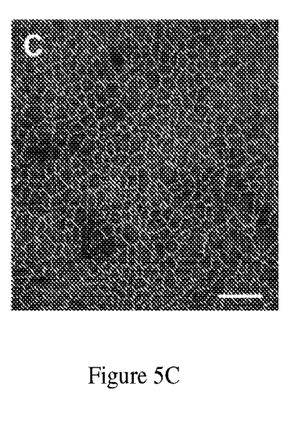

Differentiation of CECs from ocular neural crest stem cells. In order to test if CECs could be induced from the EFSC-derived NCSCs directly in vitro, NCSCs were seeded at low cell density on an FNC coated plate. After 24 hours, the culture was switched to the treatment of CEC induction (human Endothelial-SFM, 5% FBS, 0.3 mM 2-phosphate ascorbic Acid, 1% Pen/Strep) in the presence of small molecular inhibitors 1uM of SB431542 and 2.5 uM of H-1125, which suppress ALK4/5/7 and Rho-associated kinase (ROCK) signaling activities, respectively. ROCK inhibitor H-1125 was previously used instead of Y21632 to achieve a better wound healing effect on rabbit corneal endothelium injury model. The cells displayed hexagonal/polygonal morphology within one week of induction (FIG. 5A). They remained proliferative and formed a relatively homogenous monolayer of cells after a few passages (FIG. 5B). To further characterize the NCSC-derived CEC sheets, immunostaining for several typical CEC markers including tight junction protein 1 (TJP1/ZO-1), N-Cadherin, and Na+/K+ ATPase was performed (FIG. 5C). The immunostaining confirmed that the differentiated cells expressed these CEC markers including Na/K-ATPase, NCAD and ZO-1, and exhibited polygonal shapes of typical CEC morphology. The addition of small molecule H-1125, a potent ROCK inhibitor, in the differentiation medium was also found to improve the differentiation of CECs.

B. Methods

Cell Culture and Differentiation.

Human pluripotent stem cells, H9 (WA9, WiCell) and BJ-iPSC (http://grants.nih.gov/stem_cells/registry/current.htm?id=40) (passage 25-40), were cultured under feeder-free and serum-free conditions in StemPro hESC SFM medium (Carlsbad, Calif., Thermo Scientific) on plates coated with growth factor-reduced matrigel (BD Biosciences MA). After the undifferentiated hESCs reached ~80% confluence in culture, the medium was switched to serum-free N2B27 priming medium (DMEM/F12, N2, B27, 0.2% BSA, 2 mM L-GlutaMAX, 0.1 mM MEM non-essential amino acids, and 0.1 mM (3-mercaptoethanol) supplemented with 20 ng/ml bFGF for 1-2 days. The nearly confluent monolayer culture of hESCs was further cultured in N2B27 priming medium supplemented with small molecule inhibitors (5 µM SB431542, 50 nM LDN193189, and 1 µM IWP2). The medium was changed daily for six days. The PSC-derived EFSCs can be maintained and expanded in this serum-free, inhibitor-supplemented priming medium. To induce RGC differentiation from EFSCs, the cells were cultured in the priming medium supplemented with a new combination of small molecule inhibitors including 1 µM IWP2, 10 µM DAPT, and 200 nM PD173074 for over two weeks. For photoreceptor precursor differentiation, dissociated EFSCs were plated on a Matrigel-coated plate and cultured in neural induction medium as described previously (Li et al., 2011) and supplemented with 1 µM IWP2, 10 µM DAPT, and 100 nM purmorphamine for six days. Subsequently, the culture was shifted to neural induction medium supplemented with 500 nM retinoic acid and 100 µM taurine for 7 days. To induce RPE differentiation, the induction medium (GMEM, 10% knockout serum replacement, 0.1 mM MEM non-essential amino acids, 1 mM Na-Pyruvate, and 0.1 mM β-mercaptoethanol) supplemented with 10 mM nicotinamide and 100 ng/ml activin A was added to the monolayer culture of EFSCs for one week. Subsequently, the RPE precursors were matured in RPE medium, consisting of MEM-a modified medium, 5% fetal bovine serum, 2 mM L-glutamine, 0.1 mM MEM non-essential amino acids, and 1 mM Na-Pyruvate, supplemented with N1 and THT (Taurine, Hydrocortisone, Triiodo-thyronin) (Maminishkis et al., 2006). For ocular NCSC differentiation, EFSCs were plated at low density on a matrigel coated surface. The cells were cultured in neural crest induction medium (DMEM/F12: Neurobasal 50:50; N2, B27, 0.3 mM 2-phospho-L-ascorbic acid) and supplemented with 3 µM CHIR 99021. The culture was passaged when it reached about 80% confluence. To direct CEC differentiation, ocular NCSCs were seeded at low cell density on FNC Coating Mix (US Biological) coated plate. After 24 hours, the culture was switched to M5 CEC culture medium (human Endothelial-SFM, 5% FBS, 0.3 mM 2-Phosphate Ascorbic Acid, 1% Pen/Strep) supplemented with small molecular inhibitors 1 µM SB431542 and 2.5 µM H-1125 (Peh et al., 2013).

PCR Analysis.

Total RNA was extracted from cells using the RNeasy kit (Qiagen), and cDNA was reverse-transcribed using the iScript cDNA Synthesis kit (Bio-Rad, MA), both following the manufacturers' instructions. The transcripts were amplified for 40 cycles and their levels quantified using gene-specific primers and Power SYBR Green PCR Master Mix on the 7500 Real-Time PCR System (Applied Biosystems, Foster City, Calif.). Measurements were performed in triplicate and normalized to β-actin levels.

Immunocytochemistry.

Cells were fixed with 4% paraformaldehyde for 20 min, permeabilized with 0.3% Triton X-100-PBS for 5 min twice, and blocked in a solution of PBS containing 5% normal donkey serum and 0.3% TritonX-100%, followed by an overnight incubation in primary antibody solutions at 4° C. After three washes in PBS, cells were incubated with Alexa fluorescently conjugated secondary antibodies for another 90 min. After rinses and washes in PBS, cell nuclei were counterstained with 100 ng/ml Hoechst 33342 for 10 min. Primary antibodies (see Table S2) were applied and incubated over night at 4° C. The secondary antibodies used were the corresponding Alexa-488, -555, -633, or -647 fluorescent-labeled antibodies (1:1000; Life Technologies, Carlsbad, Calif.). The specific immunoreactivity of each antibody was confirmed by immunostaining using appropriate retinal tissues as positive controls under the same conditions. Labeled cells were imaged with a laser-scanning confocal microscope.

SUPPLEMENTARY TABLE S2

Primary antibodies used for immunostaining

| Antigen | Host Species | Concentration | Supplier |
|---|---|---|---|
| beta-catenin | Rabbit | 1 in 250 | Santa Cruz |
| Chx10 | Sheep | 1 in 300 | Exalpha |
| GFP | Rabbit | 1 in 1000 | Thermo Scientific |
| GFP | Chicken | 1 in 400 | Thermo Scientific |
| HNK-1 | Mouse | 1 in 200 | Sigma-Aldrich |
| Human mitochondria | Mouse | 1 in 100 | Millipore |
| Human nuclear antigen | Mouse | 1 in 300 | Millipore |
| Ki67 | Mouse | 1 in 250 | Santa Cruz |
| Lhx2 | Goat | 1 in 200 | Santa Cruz |
| Na/K-ATPase a1 | Mouse | 1 in 200 | Santa Cruz |
| N-cadherin | Mouse | 1 in 250 | Santa Cruz |
| Nestin | Goat | 1 in 350 | Santa Cruz |
| OPN1SW | Goat | 1 in 300 | Santa Cruz |
| p75NTR | Rabbit | 1 in 1600 | Cell Signaling |

SUPPLEMENTARY TABLE S2-continued

Primary antibodies used for immunostaining

| Antigen | Host Species | Concentration | Supplier |
|---|---|---|---|
| Pax6 | Rabbit | 1 in 600 | Covance |
| Recoverin | Rabbit | 1 in 2000 | Millipore |
| Red/green Opsin | Rabbit | 1 in 300 | Millipore |
| Rhodopsin | Mouse | 1 in 250 | Millipore |
| TRA-1-85 | Mouse | 1 in 100 | R&D Systems |
| ZO-1 | Rabbit | 1 in 250 | Thermo Scientific |

C. Discussion

Figure 6:
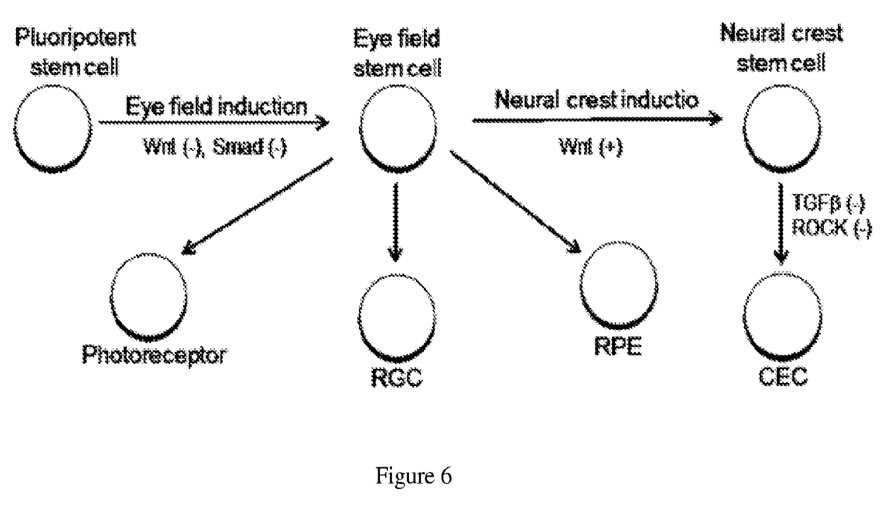
FIG. 6 is a simplified schematic of small molecule-driven fate restriction of major cell types of eye.

In this study, a small molecule-based guidance protocol was developed to generate eye field stem cells defined by the expression of multiple early eye field transcription factor genes (PAX6, LHX2, and SIX6) and by its ability to further differentiate into retinal cells (RPE, photoreceptors, and RGCs) and ocular NCSCs. It was shown that ocular NCSCs can be converted into corneal endothelial cells, which express typical markers (Na/K ATPase, ZO-1 and NCAD). Eye development and ocular cell fate restriction is a complex process involving selective activation and inhibition of multiple signaling pathways during development (del Barco Barrantes et al., 2003; Cavodeassi et al., 2005; Meyer et al., 2009; Reh et al., 2010). The approach of the present disclosure used small molecules to target these pathways (FIG. 6). For example, simultaneous inhibition of TGFβ, BMP and WNT signaling results in significant elevation of gene expression of early eye field transcription factors. An increase of WNT signaling in the ocular niche environment is important for the formation of neural crest during eye development. Previous studies on fate maps in bird and mammalian eyes demonstrated that the corneal endothelium is derived solely from neural crest cells (Gage et al., 2005; Zhang et al., 2014). This disclosure demonstrates the feasibility of using EFSC-derived NCSC as a source cell for the direct induction of CEC in culture. During eye development, the separation of lens from the surface ectoderm is an important step prior to the cornea formation (Tuft and Coster, 1990). This separation may lead to reduced signaling activity of growth factors such as FGF2 and TGFβ. That is why FGF2 was omitted from the culture medium and TGFβ pathway signaling was suppressed with SB43542 during the in vitro CEC induction from NCSC. In addition, Okumura and colleagues recently demonstrated that inhibition of the ROCK signaling pathway with ROCK inhibitor Y-27632 resulted in inhibition of apoptosis, increased proliferation of corneal endothelial cells (CECs) and enhanced corneal endothelial wound healing in vitro and in vivo (Okumura et al., 2009, 2011). It was also observed that H-1152, a potent ROCK inhibitor, exhibited more significant stimulatory effect on CEC migration, proliferation and wound healing. Therefore, H-1152 was used instead of Y-27632 to block ROCK activity during CEC induction and expansion in vitro.

The optic organoid-based differentiation methods (Eiraku et al., 2011b; Meyer et al., 2009, 2011; Nakano et al., 2012) could generate an embryonic retinal structure and provide an excellent model for studying eye development and disease modeling. Nevertheless, the 3D retinal structure is the mixture of different types of retinal cells. Additional separation procedures must be carried out to obtain a specific type of eye cells. Thus, the present work represents an alternative approach to induce a specific type of eye cells directly in a robust and scalable way. Moreover, non-retinal type of ocular cells such as CECs can de directly induced from EFSC-derived NCSCs in vitro. Unlike previous reported attempts (McCabe et al., 2015; Zhang et al., 2014), which relied on spontaneous differentiation and conditioned medium to generate CECs, the methods of the present disclosure recapitulate the developmental process of CEC cell fate specification. Using this strategy, EFSC-derived NCSCs were converted to a relatively homogenous and expandable monolayer of CECs in culture. The characteristic morphology of CEC sheet and the expression of CEC-specific proteins were observed.

D. References

1. Adelmann, H. B. (1936). The Problem of Cyclopia. Part I. Q. Rev. Biol. 11, 161-182.
2. Austin, C. P., Feldman, D. E., Ida, J. A., and Cepko, C. L. (1995). Vertebrate retinal ganglion cells are selected from competent progenitors by the action of Notch. Dev. Camb. Engl. 121, 3637-3650.
3. Banin, E., Obolensky, A., Idelson, M., Hemo, I., Reinhardtz, E., Pikarsky, E., Ben-Hur, T., and Reubinoff, B. (2006). Retinal incorporation and differentiation of neural precursors derived from human embryonic stem cells. Stem Cells Dayt. Ohio 24, 246-257.
4. Del Barco Barrantes, I., Davidson, G., Gröne, H.-J., Westphal, H., and Niehrs, C. (2003). Dkk1 and noggin cooperate in mammalian head induction. Genes Dev. 17, 2239-2244.
5. Buchholz, D. E., Hikita, S. T., Rowland, T. J., Friedrich, A. M., Hinman, C. R., Johnson, L. V., and Clegg, D. O. (2009). Derivation of functional retinal pigmented epithelium from induced pluripotent stem cells. Stem Cells Dayt. Ohio 27, 2427-2434.
6. Cavodeassi, F., Carreira-Barbosa, F., Young, R. M., Concha, M. L., Allende, M. L., Houart, C., Tada, M., and Wilson, S. W. (2005). Early stages of zebrafish eye formation require the coordinated activity of Wnt1 1, Fz5, and the Wnt/beta-catenin pathway. Neuron 47, 43-56.
7. Chambers, S. M., Fasano, C. A., Papapetrou, E. P., Tomishima, M., Sadelain, M., and Studer, L. (2009). Highly efficient neural conversion of human ES and iPS cells by dual inhibition of SMAD signaling. Nat. Biotechnol. 27, 275-280.
8. Chambers, S. M., Mica, Y., Lee, G., Studer, L., and Tomishima, M. J. (2013). Dual-SMAD Inhibition/WNT Activation-Based Methods to Induce Neural Crest and Derivatives from Human Pluripotent Stem Cells. Methods Mol. Biol. Clifton N. J.
9. Chen, B., Dodge, M. E., Tang, W., Lu, J., Ma, Z., Fan, C.-W., Wei, S., Hao, W., Kilgore, J., Williams, N. S., et al. (2009). Small molecule-mediated disruption of Wnt-dependent signaling in tissue regeneration and cancer. Nat Chem Biol 5, 100-107.
10. Czekaj, M., Haas, J., Gebhardt, M., Müller-Reichert, T., Humphries, P., Farrar, J., Bartsch, U., and Ader, M. (2012). In vitro expanded stem cells from the developing retina fail to generate photoreceptors but differentiate into myelinating oligodendrocytes. PloS One 7, e41798.
11. Eiraku, M., Takata, N., Ishibashi, H., Kawada, M., Sakakura, E., Okuda, S., Sekiguchi, K., Adachi, T., and Sasai, Y. (2011a). Self-organizing optic-cup morphogenesis in three-dimensional culture. Nature 472, 51-56.
12. Eiraku, M., Takata, N., Ishibashi, H., Kawada, M., Sakakura, E., Okuda, S., Sekiguchi, K., Adachi, T., and Sasai, Y. (2011b). Self-organizing optic-cup morphogenesis in three-dimensional culture. Nature 472, 51-56.
13. Eisenfeld, A. J., Bunt-Milam, A. H., and Saari, J. C. (1985). Immunocytochemical localization of interphotoreceptor retinoid-binding protein in developing normal and RCS rat retinas. Invest. Ophthalmol. Vis. Sci. 26, 775-778.
14. Fuhrmann, S., Levine, E. M., and Reh, T. A. (2000). Extraocular mesenchyme patterns the optic vesicle during early eye development in the embryonic chick. Dev. Camb. Engl. 127, 4599-4609.
15. Gonzalez-Cordero, A., West, E. L., Pearson, R. A., Duran, Y., Carvalho, L. S., Chu, C. J., Naeem, A., Blackford, S. J. I., Georgiadis, A., Lakowski, J., et al. (2013). Photoreceptor precursors derived from three-dimensional embryonic stem cell cultures integrate and mature within adult degenerate retina. Nat. Biotechnol. 31, 741-747.
16. Hashimoto, T., Zhang, X.-M., Chen, B. Y., and Yang, X.-J. (2006). VEGF activates divergent intracellular signaling components to regulate retinal progenitor cell proliferation and neuronal differentiation. Dev. Camb. Engl. 133, 2201-2210.
17. Idelson, M., Alper, R., Obolensky, A., Ben-Shushan, E., Hemo, I., Yachimovich-Cohen, N., Khaner, H., Smith, Y., Wiser, O., Gropp, M., et al. (2009). Directed Differentiation of Human Embryonic Stem Cells into Functional Retinal Pigment Epithelium Cells. Cell Stem Cell 5, 396-408.
18. Klimanskaya, I., Hipp, J., Rezai, K. A., West, M., Atala, A., and Lanza, R. (2004). Derivation and comparative assessment of retinal pigment epithelium from human embryonic stem cells using transcriptomics. Cloning Stem Cells 6, 217-245.
19. Kriks, S., Shim, J.-W., Piao, J., Ganat, Y. M., Wakeman, D. R., Xie, Z., Carrillo-Reid, L., Auyeung, G., Antonacci, C., Buch, A., et al. (2011). Dopamine neurons derived from human ES cells efficiently engraft in animal models of Parkinson's disease. Nature 480, 547-551.
20. Lamba, D. A., Karl, M. O., Ware, C. B., and Reh, T. A. (2006). Efficient generation of retinal progenitor cells from human embryonic stem cells. Proc. Natl. Acad. Sci. U.S.A 103, 12769-12774.
21. Lamba, D. A., McUsic, A., Hirata, R. K., Wang, P.-R., Russell, D., and Reh, T. A. (2010). Generation, purification and transplantation of photoreceptors derived from human induced pluripotent stem cells. PloS One 5, e8763.
22. Lee, G., Kim, H., Elkabetz, Y., Al Shamy, G., Panagiotakos, G., Barberi, T., Tabar, V., and Studer, L. (2007). Isolation and directed differentiation of neural crest stem cells derived from human embryonic stem cells. Nat. Biotechnol. 25, 1468-1475.
23. Li, H., Tierney, C., Wen, L., Wu, J. Y., and Rao, Y. (1997). A single morphogenetic field gives rise to two retina primordia under the influence of the prechordal plate. Dev. Camb. Engl. 124, 603-615.
24. Li, W., Sun, W., Zhang, Y., Wei, W., Ambasudhan, R., Xia, P., Talantova, M., Lin, T., Kim, J., Wang, X., et al. (2011). Rapid induction and long-term self-renewal of primitive neural precursors from human embryonic stem cells by small molecule inhibitors. Proc. Natl. Acad. Sci. U.S.A 108, 8299-8304.
25. Maminishkis, A., Chen, S., Jalickee, S., Banzon, T., Shi, G., Wang, F. E., Ehalt, T., Hammer, J. A., and Miller, S. S. (2006). Confluent monolayers of cultured human fetal retinal pigment epithelium exhibit morphology and physiology of native tissue. Invest. Ophthalmol. Vis. Sci. 47, 3612-3624.
26. McCabe, K. L., Kunzevitzky, N. J., Chiswell, B. P., Xia, X., Goldberg, J. L., and Lanza, R. (2015). Efficient Generation of Human Embryonic Stem Cell-Derived Corneal Endothelial Cells by Directed Differentiation. PLoS ONE 10, e0145266.
27. Meyer, J. S., Shearer, R. L., Capowski, E. E., Wright, L. S., Wallace, K. A., McMillan, E. L., Zhang, S.-C., and Gamm, D. M. (2009). Modeling early retinal development with human embryonic and induced pluripotent stem cells. Proc. Natl. Acad. Sci. U.S.A 106, 16698-16703.
28. Meyer, J. S., Howden, S. E., Wallace, K. A., Verhoeven, A. D., Wright, L. S., Capowski, E. E., Pinilla, I., Martin, J. M., Tian, S., Stewart, R., et al. (2011). Optic Vesicle-like Structures Derived from Human Pluripotent Stem Cells Facilitate a Customized Approach to Retinal Disease Treatment. STEM CELLS 29, 1206-1218.
29. Müller, F., Rohrer, H., and Vogel-Hopker, A. (2007). Bone morphogenetic proteins specify the retinal pigment epithelium in the chick embryo. Dev. Camb. Engl. 134, 3483-3493.
30. Nakano, T., Ando, S., Takata, N., Kawada, M., Muguruma, K., Sekiguchi, K., Saito, K., Yonemura, S., Eiraku, M., and Sasai, Y. (2012). Self-formation of optic cups and storable stratified neural retina from human ESCs. Cell Stem Cell 10, 771-785.
31. Okumura, N., Ueno, M., Koizumi, N., Sakamoto, Y., Hirata, K., Hamuro, J., and Kinoshita, S. (2009). Enhancement on primate corneal endothelial cell survival in vitro by a ROCK inhibitor. Invest. Ophthalmol. Vis. Sci. 50, 3680-3687.
32. Okumura, N., Koizumi, N., Ueno, M., Sakamoto, Y., Takahashi, H., Hirata, K., Torii, R., Hamuro, J., and Kinoshita, S. (2011). Enhancement of corneal endothelium wound healing by Rho-associated kinase (ROCK) inhibitor eye drops. Br. J. Ophthalmol. 95, 1006-1009.
33. Osakada, F., Ikeda, H., Mandai, M., Wataya, T., Watanabe, K., Yoshimura, N., Akaike, A., Akaike, A., Sasai, Y., and Takahashi, M. (2008). Toward the generation of rod and cone photoreceptors from mouse, monkey and human embryonic stem cells. Nat. Biotechnol. 26, 215-224.
34. Peh, G. S. L., Chng, Z., Ang, H. P., Cheng, T. Y. D., Adnan, K., Seah, X. Y., George, B. L., Toh, K. P., Tan, D. T., Yam, G. H. F., et al. (2013). Propagation of Human Corneal Endothelial Cells: A Novel Dual Media Approach. Cell Transplant.
35. Reh, T. A., Lamba, D., and Gust, J. (2010). Directing human embryonic stem cells to a retinal fate. Methods Mol. Biol. Clifton N. J. 636, 139-153.
36. Schwartz, S. D., Hubschman, J.-P., Heilwell, G., Franco-Cardenas, V., Pan, C. K., Ostrick, R. M., Mickunas, E., Gay, R., Klimanskaya, I., and Lanza, R. (2012). Embryonic stem cell trials for macular degeneration: a preliminary report. Lancet 379, 713-720.
37. Schwartz, S. D., Regillo, C. D., Lam, B. L., Eliott, D., Rosenfeld, P. J., Gregori, N. Z., Hubschman, J.-P., Davis, J. L., Heilwell, G., Spirn, M., et al. (2015). Human embryonic stem cell-derived retinal pigment epithelium in patients with age-related macular degeneration and Stargardt's macular dystrophy: follow-up of two open-label phase 1/2 studies. Lancet Lond. Engl. 385, 509-516.
38. Sinha, S., and Chen, J. K. (2006). Purmorphamine activates the Hedgehog pathway by targeting Smoothened. Nat. Chem. Biol. 2, 29-30.
39. Tuft, S. J., and Coster, D. J. (1990). The corneal endothelium. Eye Lond. Engl. 4 (Pt 3), 389-424.

40. Vugler, A., Carr, A.-J., Lawrence, J., Chen, L. L., Burrell, K., Wright, A., Lundh, P., Semo, M., Ahmado, A., Gias, C., et al. (2008). Elucidating the phenomenon of HESC-derived RPE: anatomy of cell genesis, expansion and retinal transplantation. Exp. Neurol. 214, 347-361.
41. Yokoyama, T., Liou, G. I., Caldwell, R. B., and Overbeek, P. A. (1992). Photoreceptor-specific activity of the human interphotoreceptor retinoid-binding protein (IRBP) promoter in transgenic mice. Exp. Eye Res. 55, 225-233.
42. Zarbin, M. (2016). Cell-Based Therapy for Degenerative Retinal Disease. Trends Mol. Med. 22, 115-134.
43. Zhang, K., Pang, K., and Wu, X. (2014). Isolation and transplantation of corneal endothelial cell-like cells derived from in-vitro-differentiated human embryonic stem cells. Stem Cells Dev. 23, 1340-1354.
44. Zuber, M. E., Gestri, G., Viczian, A. S., Barsacchi, G., and Harris, W. A. (2003). Specification of the vertebrate eye by a network of eye field transcription factors. Dev. Camb. Engl. 130, 5155-5167.

The invention claimed is:

1. A method of culturing corneal endothelial cells (CECs) in vitro comprising:
   a. providing a culture of pluripotent stem cells (PSCs),
   b. culturing the PSCs with a culture medium containing WNT pathway signaling inhibitor, a BMP pathway signaling inhibitor, and a TGF-β pathway signaling inhibitor for a time period sufficient to produce a culture of eye field stem cells (EFSCs), wherein the culture of EFSCs comprises 70% or more EFSCs,
   c. removing EFSC medium and replacing with a culture medium that lacks the WNT pathway signaling inhibitor and promoting WNT signaling in the EFSCs by removal of EFSC media from the EFSCs to produce a culture of ocular neural crest stem cells (NCSCs), and then
   d. changing the culture medium of the NCSCs to one that includes the TGF-β pathway signaling inhibitor and a ROCK signaling inhibitor suppressing TGF-β pathway signaling and ROCK signaling in the culture of NCSCs, thereby producing a culture of culturing CECs;
   wherein the WNT pathway signaling inhibitor is IWP2, the BMP pathway signaling inhibitor is LDN193189, and the TGF-β pathway signaling inhibitor is SB431542.

2. The method of claim 1, wherein the step of suppressing TGFβ and ROCK signaling is conducted in a feeder-free and serum-free defined media by applying a small molecule differentiator to the culture.

3. The method of claim 2, wherein the small molecule differentiator comprises a ROCK inhibitor and a TGFβ inhibitor.

4. The method of claim 3, wherein the ROCK inhibitor is H-1125 or Y27632, and wherein the TGFβ inhibitor is SB431542.

5. The method of claim 1, wherein the CEC culture is expanded into a sheet of cells.

6. The method of claim 1, wherein the majority of NCSCs express neural crest markers p75NTR and HNK-1.

7. The method of claim 1, wherein the majority of EFSCs express markers PAX6 and LHX2.

* * * * *